(12) United States Patent
Seiler et al.

(10) Patent No.: US 10,058,453 B2
(45) Date of Patent: Aug. 28, 2018

(54) EXTRACTING LENTICULES FOR REFRACTIVE CORRECTION

(75) Inventors: Theo Seiler, Zurich (CH); Katrin Skerl, Erlangen (DE); Jörg Klenke, Nürnberg (DE)

(73) Assignee: Wavelight GmbH (DE)

( * ) Notice: Subject to any disclaimer, the term of this patent is extended or adjusted under 35 U.S.C. 154(b) by 478 days.

(21) Appl. No.: 13/454,468

(22) Filed: Apr. 24, 2012

(65) Prior Publication Data

US 2013/0281992 A1  Oct. 24, 2013

(51) Int. Cl.
*A61B 18/20* (2006.01)
*A61F 9/008* (2006.01)

(52) U.S. Cl.
CPC ...... *A61F 9/00827* (2013.01); *A61F 2009/00872* (2013.01); *A61F 2009/00897* (2013.01)

(58) Field of Classification Search
CPC ............ A61F 9/013; A61F 2009/00827; A61F 2009/00872; A61F 2009/00897
USPC .......................................................... 606/5
See application file for complete search history.

(56) References Cited

U.S. PATENT DOCUMENTS

| | | | |
|---|---|---|---|
| 7,351,241 B2 * | 4/2008 | Bendett ............... | A61F 9/00827 128/898 |
| 2002/0151878 A1 * | 10/2002 | Shimmick et al. ............... | 606/5 |
| 2003/0212387 A1 * | 11/2003 | Kurtz ...................... | A61F 9/008 606/4 |
| 2004/0243111 A1 | 12/2004 | Bendett et al. | |
| 2007/0129742 A1 * | 6/2007 | McDonald .................... | 606/166 |
| 2008/0275433 A1 * | 11/2008 | Russmann et al. ............... | 606/5 |
| 2008/0319464 A1 * | 12/2008 | Bischoff et al. .............. | 606/166 |
| 2009/0069817 A1 | 3/2009 | Peyman | |
| 2010/0049174 A1 * | 2/2010 | Kuehnert et al. .................. | 606/4 |
| 2010/0262128 A1 * | 10/2010 | Vogler ................ | A61F 9/00827 606/4 |
| 2010/0331830 A1 | 12/2010 | Bischoff et al. | |
| 2010/0331831 A1 * | 12/2010 | Bischoff et al. .................. | 606/5 |
| 2011/0160710 A1 * | 6/2011 | Frey et al. ........................ | 606/6 |
| 2012/0016353 A1 | 1/2012 | Bissmann | |

FOREIGN PATENT DOCUMENTS

| | | | |
|---|---|---|---|
| DE | 102007019813 A1 | 10/2008 | |
| DE | 102007053281 A1 | 5/2009 | |
| DE | 102008049401 A1 * | 4/2010 | ............. A61F 9/008 |
| DE | 102009014911 A1 | 10/2010 | |

(Continued)

OTHER PUBLICATIONS

Young, International Outlook; Lenticule may beat LASIK in the dry eye arena; Matt Young EyeWorld Contributing Editor; pp. 1-3; Date published on-line: Feb. 2012; http://eyeworld.org/printarticle.php?id=6223.

(Continued)

*Primary Examiner* — Boniface N Nganga
(74) *Attorney, Agent, or Firm* — Keiko Ichiye

(57) ABSTRACT

In certain embodiments, refractive correction includes controlling a focus of pulsed laser radiation having ultrashort pulses. A channel is created with the pulsed laser radiation to facilitate separation of the lenticule from the eye. A posterior incision is created with the pulsed laser radiation to form a posterior side of the lenticule. An anterior incision is created with the pulsed laser radiation to form an anterior side of the lenticule.

14 Claims, 3 Drawing Sheets

(56) References Cited

FOREIGN PATENT DOCUMENTS

JP          2011-507559 T2    3/2011
RU            2469689 C2   12/2012

OTHER PUBLICATIONS

Zeiss; Carl Zeiss Meditec; Femtosecond Lenticule Extraction (FLEx) and Other Exciting Applications of Femtosecond Lasers—New approaches to cornea and lens laser surgery; Manfred Dick; Hartmut Vogelsang; Walter Sekundo, Markus Blum; San Francisco, 2008.

* cited by examiner

EXTRACTING LENTICULES FOR REFRACTIVE CORRECTION

TECHNICAL FIELD

The present disclosure relates generally to corneal surgical devices, and more particularly to extracting lenticules for refractive correction.

BACKGROUND

Refractive surgery uses lasers to reshape the cornea to correct refractive defects of the eye. According to some techniques, a flap of the eye is lifted to expose a portion of the cornea that is reshaped by ablation using an excimer laser. The flap is then replaced. According to other techniques, a femtosecond laser makes incisions in the cornea to create a lenticule. The lenticule is removed to reshape the cornea.

BRIEF SUMMARY

In certain embodiments, a device for refractive correction comprises a laser device and a control computer. The laser device is configured to create a lenticule in an eye using pulsed laser radiation having ultrashort pulses. The laser device includes one or more controllable components configured to control a focus of the pulsed laser radiation. The control computer is configured to instruct the one or more controllable components to create a channel with the pulsed laser radiation to facilitate separation of the lenticule from the eye, create a posterior incision with the pulsed laser radiation to form a posterior side of the lenticule, and create an anterior incision with the pulsed laser radiation to form an anterior side of the lenticule.

In certain embodiments, a method for refractive correction includes controlling a focus of pulsed laser radiation having ultrashort pulses. A channel is created with the pulsed laser radiation to facilitate separation of the lenticule from the eye. A posterior incision is created with the pulsed laser radiation to form a posterior side of the lenticule. An anterior incision is created with the pulsed laser radiation to form an anterior side of the lenticule.

In certain embodiments, a tangible computer-readable medium stores computer code for refractive correction that when executed by a computer is configured to control a focus of pulsed laser radiation having ultrashort pulses. The computer code is also configured to create a channel with the pulsed laser radiation to facilitate separation of the lenticule from the eye, create a posterior incision with the pulsed laser radiation to form a posterior side of the lenticule, and create an anterior incision with the pulsed laser radiation to form an anterior side of the lenticule.

BRIEF DESCRIPTION OF THE DRAWINGS

Exemplary embodiments of the present disclosure will now be described by way of example in greater detail with reference to the attached figures, in which.

DESCRIPTION OF EXAMPLE EMBODIMENTS

Figure 1:
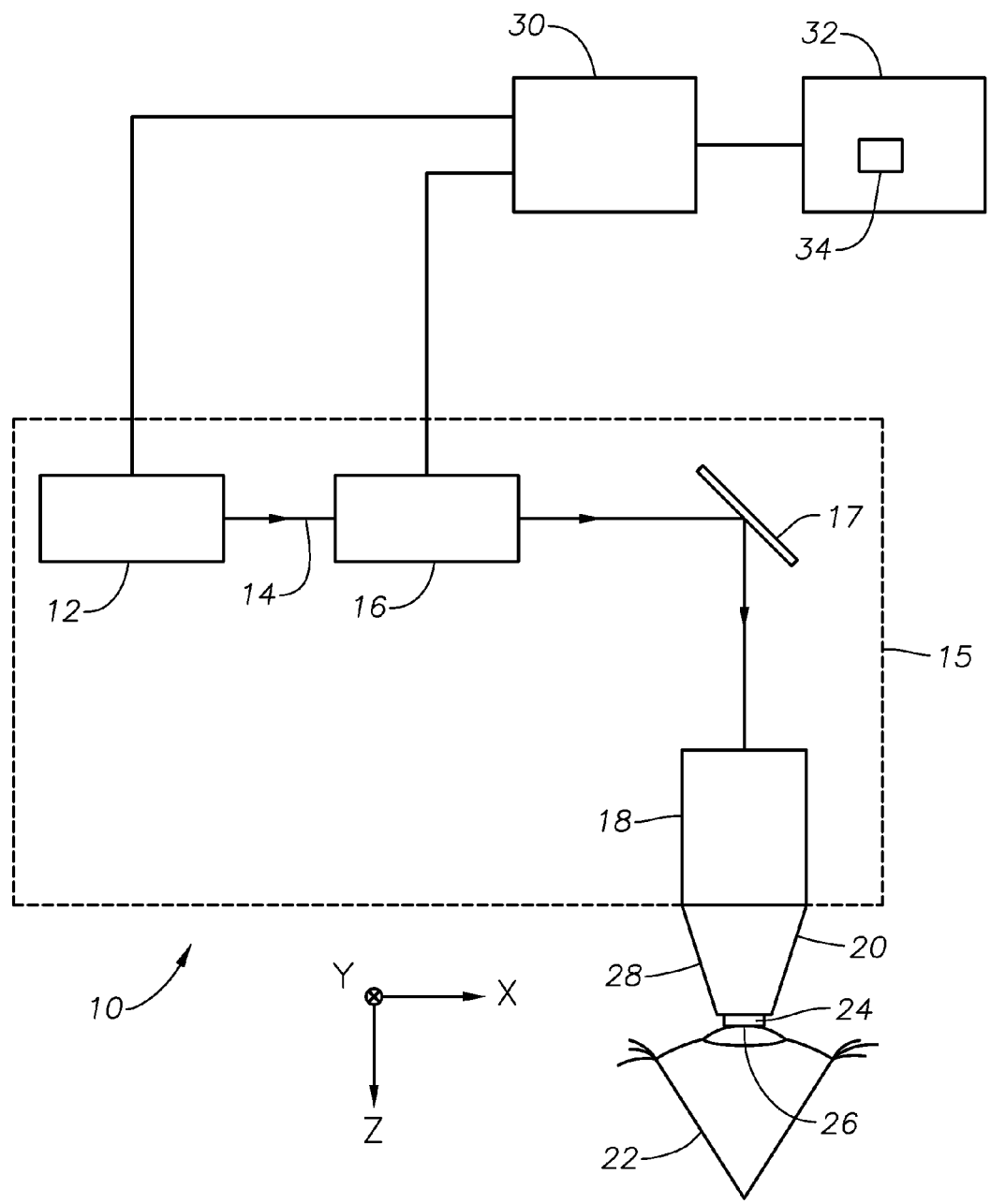
FIG. 1 illustrates an example of a device configured to perform refractive correction according to certain embodiments.

Referring now to the description and drawings, example embodiments of the disclosed apparatuses, systems, and methods are shown in detail. The description and drawings are not intended to be exhaustive or otherwise limit or restrict the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments. In addition, certain drawings may be in schematic form.

FIG. 1 illustrates an example of a device 10 configured to create a lenticule according to certain embodiments. In the embodiments, the device 10 includes a laser device and a control computer. The laser device can create a lenticule in the cornea (such as the stroma) of an eye using pulsed laser radiation with ultrashort pulses (such as pico-, femto-, or attosecond pulses). The lenticule may be shaped according to a refractive correction profile such that when the lenticule is removed the refractive correction is applied.

The laser device may include controllable components that focus the pulsed laser radiation. The control computer instructs the controllable components to focus the pulsed laser radiation at the cornea to create a channel (such as an anterior or posterior channel) to facilitate separation of the lenticule. The pulsed laser radiation may create an anterior incision to form an anterior side of the lenticule and a posterior incision to form a posterior side of the lenticule. In certain embodiments, the pulsed laser radiation may create a removal incision through which the lenticule may be manually or automatically removed.

In the illustrated example of FIG. 1, the device 10 performs surgery on an eye 22. The device 10 includes a laser device 15, a patient adapter 20, a control computer 30, and a memory 32 coupled as shown. The laser device 15 may include a laser source 12, a scanner 16, one or more optical elements 17, and/or a focusing objective 18 coupled as shown. The patient adapter 20 may include a contact element 24 (which has an abutment face 26 disposed outwardly from a sample) and a sleeve 28 coupled as shown. The memory 32 stores a control program 34. The sample may be an eye 22.

The laser source 12 generates a laser beam 14 with ultrashort pulses. In this document, an "ultrashort" pulse of light refers to a light pulse that has a duration that is less than a nanosecond, such as on the order of a picosecond, femtosecond, or attosecond. The focal point of the laser beam 14 may create a laser-induced optical breakdown (LIOB) in tissues such as the cornea. The laser beam 14 may be precisely focused to allow for precise incisions in the corneal cell layers, which may reduce or avoid unnecessary destruction of other tissue.

Examples of laser source 12 include femtosecond, picosecond, and attosecond lasers. The laser beam 14 may have any suitable wavelength, such as a wavelength in the range of 300 to 1500 nanometers (nm), for example, a wavelength in the range of 300 to 650, 650 to 1050, 1050 to 1250, or 1100 to 1500 nm. The laser beam 14 may also have a relatively small focus volume, e.g., 5 micrometers (μm) or less in diameter. In certain embodiments, the laser source 12 and/or delivery channel may be in a vacuum or near vacuum.

The scanner 16, optical elements 17, and focusing objective 18 are in the beam path. The scanner 16 transversely and longitudinally controls the focal point of the laser beam 14. "Transverse" refers to a direction at right angles to the direction of propagation of the laser beam 14, and "longitudinal" refers to the direction of beam propagation. The transverse plane may be designated as the x-y plane, and the longitudinal direction may be designated as the z-direction. In certain embodiments, the abutment face 26 of the patient interface 20 is on an x-y plane.

The scanner 16 may transversely direct the laser beam 14 in any suitable manner. For example, the scanner 16 may include a pair of galvanometrically actuated scanner mirrors that can be tilted about mutually perpendicular axes. As another example, the scanner 16 may include an electro-optical crystal that can electro-optically steer the laser beam 14. The scanner 16 may longitudinally direct the laser beam 14 in any suitable manner. For example, the scanner 16 may include a longitudinally adjustable lens, a lens of variable refractive power, or a deformable mirror that can control the z-position of the beam focus. The focus control components of the scanner 16 may be arranged in any suitable manner along the beam path, e.g., in the same or different modular units.

One (or more) optical elements 17 direct the laser beam 14 towards the focusing objective 18. An optical element 17 may be any suitable optical element that can reflect, refract, and/or diffract the laser beam 14. For example, an optical element 17 may be an immovable deviating mirror. The focusing objective 18 focuses the laser beam 14 onto the patient adapter 20, and may be separably coupled to the patient adapter 20. The focusing objective 18 may be any suitable optical element, such as an f-theta objective.

Patient adapter 20 interfaces with the cornea of the eye 22. In the example, the patient adapter 20 has a sleeve 28 coupled to a contact element 24. The sleeve 28 couples to the focusing objective 18. The contact element 24 may be translucent or transparent to the laser radiation and has an abutment face 26 that interfaces with the cornea and may level a portion of the cornea. In certain embodiments, the abutment face 26 is planar and forms a planar area on the cornea. The abutment face 26 may be on an x-y plane, so the planar area is also on an x-y plane. In other embodiments, the abutment face 26 need not be planar, e.g., may be convex or concave.

The control computer 30 controls controllable components, e.g., the laser source 12 and scanner 16, in accordance with the control program 34. The control program 34 contains computer code that instructs the controllable components to focus the pulsed laser radiation at a region of the cornea to photodisrupt at least a portion of the region.

In certain examples of operation, the scanner 16 may direct the laser beam 14 to form incisions of any suitable geometry. Examples of types of incisions include bed incisions and lateral incisions. A bed incision is two-dimensional incision that is typically on an x-y plane. The scanner 16 may form a bed incision by focusing the laser beam 14 at a constant z-value under the abutment face 26 and moving the focus in a pattern in an x-y plane. A lateral incision is an incision that extends from under the corneal surface (such as from a bed incision) to the surface. The scanner 16 may form a lateral incision by changing the z-value of the focus of the laser beam 14 and optionally changing the x and/or y values.

Any suitable portion of the cornea may be photodisrupted. One or more of any of the corneal layers may be selected for photodisruption. In addition, a portion of a cell layer may be photodisrupted in the z-direction, but part of the cell layer may remain on the cornea. Moreover, a particular area (or "target zone") in the x-y plane may be selected for photodisruption. For example, a target zone that forms a bed incision may be photodisrupted.

The device 10 may photodisrupt a corneal layer in any suitable manner. In certain embodiments, the control computer 30 may instruct the laser device to focus the laser beam 14 at a constant z-value under the abutment face 26 and move in a pattern in the x-y plane that substantially covers the target zone. Any suitable pattern may be used. For example, according to a zigzag pattern, the scan path has a constant y-value and moves in the +x direction. When the scan path reaches a point of the border of the target zone, the path moves to a next y value that is a predetermined distance from the previous y-value and then moves in the −x direction until it reaches another point of the border. The scan path continues until the entire target zone is scanned. As another example, according to a spiral pattern, the scan path starts at or near the center of the target zone and moves in a spiral pattern until the path reaches the border of the target zone, or vice-versa.

As the laser beam 14 travels along the scan path, the laser beam pulses create microdisruptions. In certain situations, a scan path pattern may yield a non-uniform distribution of microdisruptions over the target zone. In these cases, the laser beam 14 may be modified to make the distribution more uniform. For example, certain pulses may be blocked or the pulse energy may be decreased to reduce number of or the effect of the pulses in a particular region.

Figure 2:
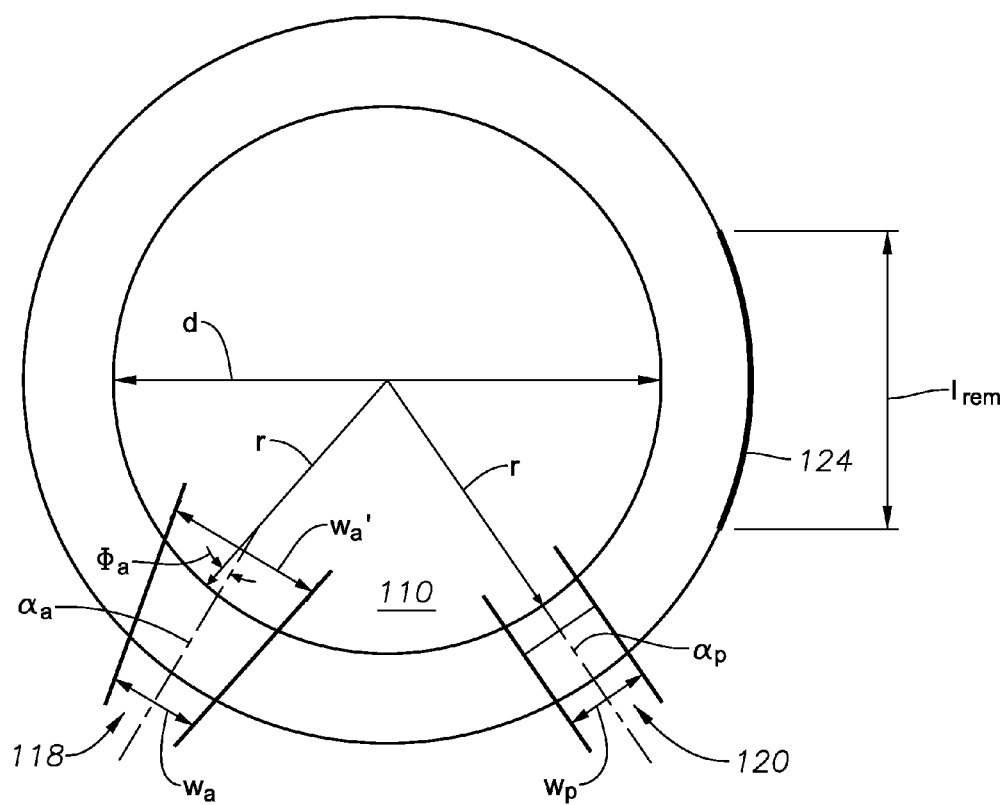
FIG. 2 illustrates a top view of an example of creating a lenticule according to certain embodiments.
Figure 3:
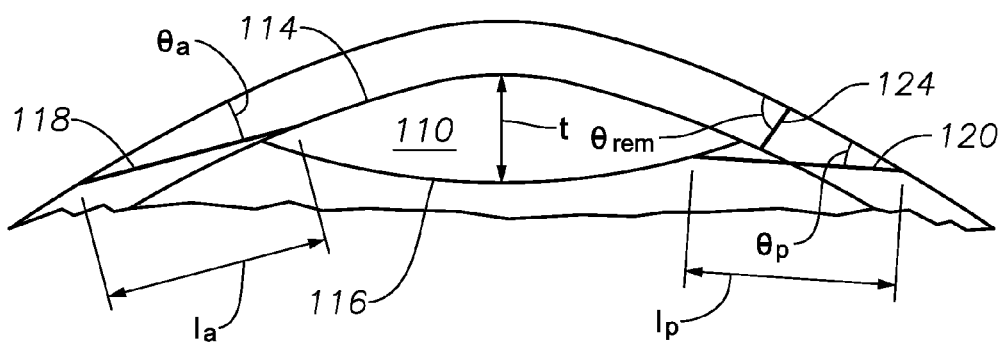
FIG. 3 illustrates a cross-section of an example of creating a lenticule according to certain embodiments.

FIGS. 2 and 3 illustrate an example of creating a lenticule 110 according to certain embodiments. FIG. 2 illustrates a top view of creating the lenticule 110, and FIG. 3 illustrates a cross-section of creating the lenticule 110.

The lenticule 110 may have any suitable shape. In certain embodiments, the lenticule 110 may have a flattened, disc shape with any suitable perimeter, e.g., a circular, elliptical, free form, or irregular. The lenticule 110 may have any suitable size. For example, the lenticule 110 may have any suitable diameter d (or radius r), such as a diameter d in the range of 1 to 10 mm, such as approximately 6.5 mm. The lenticule 110 may have any suitable thickness t, such as a value in the range of 10 to 200 micrometers ($\mu$m), such as approximately 50 $\mu$m.

The device 10 may create the lenticule 110 in any suitable manner. In certain embodiments, the control computer 30 may instruct the laser device to create an anterior incision 114 and a posterior incision 116, which are types of bed incisions, using laser radiation. The anterior incision 114 forms the anterior side of the lenticule 110, and the posterior incision 116 forms the posterior side of the lenticule 110. In certain embodiments, the anterior incision 114 and/or posterior incision 116 yields a refractive profile for refractive correction such that a refractive correction is applied after removal of the lenticule 110.

The anterior 114 and posterior 116 incisions may be created in any suitable order and in any suitable manner. In certain embodiments, a channel, which may be a type of lateral incision, may facilitate removal of the lenticule 110. For example, an anterior channel 118 may be used to separate the anterior side of the lenticule 110 from the surrounding tissue, and/or a posterior channel 120 may be used to separate the posterior side of the lenticule 110 from the surrounding tissue. In the embodiments, the channel may be used to insert (e.g., manually or automatically) an instrument into an incision to separate a surface of the lenticule 110 from the rest of the cornea in order to remove the lenticule 110.

The channels and incisions may be created in any suitable order. For example, a channel may be created before or after the corresponding incision. As another example, an anterior channel and/or anterior incision may be created before or after a posterior channel and/or posterior incision.

A channel may have any suitable size and shape. In certain embodiments, a channel with a center line $\alpha_i$, where i identifies the channel, may have any suitable length $l_i$, width $w_i$, angle $\Phi_i$ of center line $\alpha_i$ with respect to radius r, and angle $\theta_i$ of center line $\alpha_i$ with respect to the anterior surface of the eye. In FIG. 2, the anterior channel 118 has a narrower width $w_a$ towards the entrance of the channel and a wider width $w_a'$ towards the center of lenticule 110. The posterior channel 120 has the same width $w_p$ from end to end. The widths may have any suitable value, such as a value in the range 0.5 to 4, 1 to 3, or 1.5 to 2.0 mm. In other examples, the posterior channel may be shaped like channel 118 or may have any other suitable shape, and the anterior channel may be shaped like channel 120 or may have any other suitable shape. The posterior and anterior channels may have the same shape or may have different shapes. The center line $\alpha_a$ of the anterior channel 118 is at an angle $\Phi_a$ with respect to radius r. The center line $\alpha_p$ of the posterior channel 120 is at an angle $\Phi_p$ (not labeled) of 0° with respect to radius r. The angles $\Phi_i$ may have any suitable value, such as a value in the range 0 to 5, 5 to 10, 10 to 15, or 15 to 20 degrees.

The channels and incisions may be created in any suitable order. For example, a channel may be created before or after the corresponding incision. As another example, an anterior channel and/or anterior incision may be created before or after a posterior channel and/or posterior incision.

In FIG. 3, the anterior channel 118 has length $l_a$, and the posterior channel 120 has length $l_p$. The lengths may have any suitable value, such as a value in the range 1 to 5 mm. The center line $\alpha_a$ of anterior channel 118 has an angle $\theta_a$ with respect to the surface of the eye, and the center line $\alpha_p$ of posterior channel 120 has an angle $\theta_p$. The angles $\theta_i$ may have any suitable value, such as a value where the channel is substantially tangential or nearly tangential (within 5 degrees) to the corresponding incision to allow for an instrument that is inserted into the channel to enter the incision and separate a surface of the lenticule from the rest of the cornea. For example, angles $\theta_i$ may have a value in the range 0 to 10, 10 to 20, or 20 to 30 degrees, which may allow the channels to be tangential or nearly tangential to a surface of the lenticule. In certain embodiments, the angles $\theta_i$ may have different values at the entrance of the eye (e.g., approximately 90 degrees) and then change to values that allow the channels to be tangential or nearly tangential to a surface of the lenticule.

The lenticule 110 may be removed in any suitable manner. In certain embodiments, the lenticule 110 may be extracted through an anterior incision or posterior incision. In other embodiments, the control computer 30 may instruct the laser device to form a removal incision through which the lenticule 110 may be manually or automatically extracted. The removal incision 124 may have any suitable size or shape. In certain embodiments, the removal incision 124 may have any suitable length $l_{rem}$ and angle $\theta_{rem}$ with respect to the surface of the eye. For example, length $l_{rem}$ may have a value that allows for the lenticule 110 to be extracted through it, such as a value that is approximately the size of diameter d, but perhaps up to 2 mm larger or smaller. Angle $\theta_{rem}$ may have a value in the range of 80 to 110 degrees.

Figure 4:
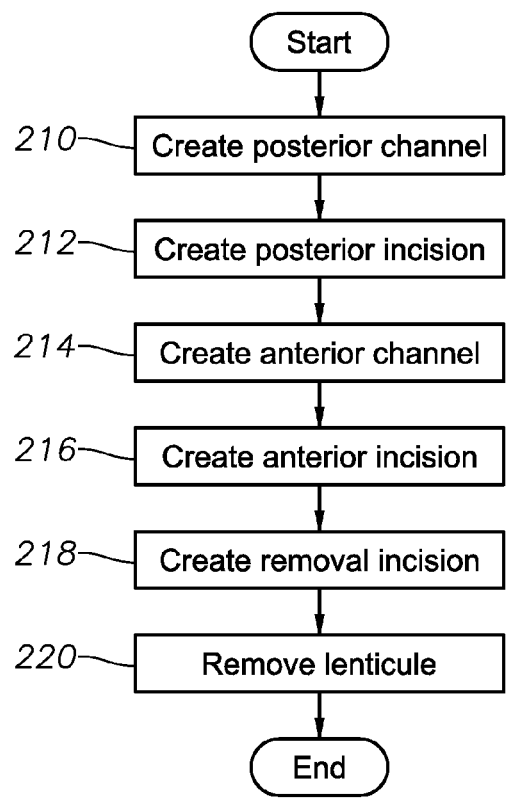
FIG. 4 illustrates an example of a method for creating a lenticule according to certain embodiments.

FIG. 4 illustrates an example of a method for creating a lenticule in a cornea of an eye according to certain embodiments. The method may be performed by the system 10 of FIG. 1.

The method starts at step 210, where a posterior channel 120 is created. The posterior channel 120 may be used to separate the posterior side of the lenticule 110 from the rest of the eye. A posterior incision 116 is created at step 212. The posterior incision 116 forms a posterior surface of the lenticule 110. An anterior channel 118 is created at step 214. The anterior channel 118 may be used to separate the anterior side of the lenticule 110 from the rest of the eye. An anterior incision 114 is created at step 216. The anterior incision 114 forms an anterior surface of the lenticule 110.

A removal incision 124 is created at step 218. The removal incision 124 allows for the removal of the lenticule 110. The lenticule 110 is removed through the removal incision 124 at step 220. The lenticule 110 may be manually or automatically removed. In other embodiments, the lenticule 110 may be removed through the anterior 118 or posterior 120 channel.

A component (such as the control computer 30) of the systems and apparatuses disclosed herein may include an interface, logic, memory, and/or other suitable element, any of which may include hardware and/or software. An interface can receive input, send output, process the input and/or output, and/or perform other suitable operations. Logic can perform the operations of a component, for example, execute instructions to generate output from input. Logic may be encoded in memory and may perform operations when executed by a computer. Logic may be a processor, such as one or more computers, one or more microprocessors, one or more applications, and/or other logic. A memory can store information and may comprise one or more tangible, computer-readable, and/or computer-executable storage medium. Examples of memory include computer memory (for example, Random Access Memory (RAM) or Read Only Memory (ROM)), mass storage media (for example, a hard disk), removable storage media (for example, a Compact Disk (CD) or a Digital Video or Versatile Disk (DVD)), database and/or network storage (for example, a server), and/or other computer-readable media.

In particular embodiments, operations of the embodiments may be performed by one or more computer readable media encoded with a computer program, software, computer executable instructions, and/or instructions capable of being executed by a computer. In particular embodiments, the operations may be performed by one or more computer readable media storing, embodied with, and/or encoded with a computer program and/or having a stored and/or an encoded computer program.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

Other modifications are possible without departing from the scope of the invention. For example, the description illustrates embodiments in particular practical applications, yet other applications will be apparent to those skilled in the art. In addition, future developments will occur in the arts discussed herein, and the disclosed systems, apparatuses, and methods will be utilized with such future developments.

The scope of the invention should not be determined with reference to the description. In accordance with patent statutes, the description explains and illustrates the principles and modes of operation of the invention using exemplary embodiments. The description enables others skilled in the art to utilize the systems, apparatuses, and methods in various embodiments and with various modifications, but should not be used to determine the scope of the invention.

The scope of the invention should be determined with reference to the claims and the full scope of equivalents to which the claims are entitled. All claims terms should be given their broadest reasonable constructions and their ordinary meanings as understood by those skilled in the art, unless an explicit indication to the contrary is made herein. For example, use of the singular articles such as "a," "the," etc. should be read to recite one or more of the indicated elements, unless a claim recites an explicit limitation to the contrary. As another example, "each" refers to each member of a set or each member of a subset of a set, where a set may include zero, one, or more than one element. In sum, the invention is capable of modification, and the scope of the invention should be determined, not with reference to the description, but with reference to the claims and their full scope of equivalents.

What is claimed is:

1. A method for refractive correction, the method comprising:
   controlling, by one or more controllable components of a laser device, a focus of pulsed laser radiation to create a lenticule in an eye, the pulsed laser radiation having a plurality of ultrashort pulses;
   creating a straight posterior channel having a length between 1 to 5 millimeters with the pulsed laser radiation;
   creating a posterior incision with the pulsed laser radiation to form a posterior side of the lenticule, the posterior channel substantially tangential to the posterior incision to facilitate separation of the posterior side of the lenticule from the eye;
   creating a straight anterior channel having a length between 1 to 5 millimeters with the pulsed laser radiation;
   creating an anterior incision with the pulsed laser radiation to form an anterior side of a lenticule, the anterior channel substantially tangential to the anterior incision to facilitate separation of the anterior side of the lenticule from the eye, the anterior channel disconnected from the posterior side of the lenticule, the posterior channel disconnected from the anterior side of the lenticle;
   creating the anterior incision and the posterior incision yielding a refractive profile for refractive correction; and
   creating one of the anterior channel or the posterior channel with the same width at each end and create the other of the anterior channel or the posterior channel with different widths at each end.

2. The method of claim 1, creating the posterior channel further comprising:
   creating the posterior channel that has the same width at each end.

3. The method of claim 1, creating the anterior channel further comprising:
   creating the anterior channel that has different widths at each end.

4. The method of claim 1, further comprising:
   creating a removal incision with the pulsed laser radiation to facilitate removal of the lenticule from the eye.

5. The method of claim 1, the channel having an angle with respect to a surface of the eye that is between zero and 20 degrees.

6. The method of claim 1, an ultrashort pulse having a pulse that is less than one (1) nanosecond.

7. The method of claim 1, further comprising:
   controlling, by the one or more controllable components, the focus of pulsed laser radiation to have a focus volume with a diameter of 5 micrometers or less.

8. The method of claim 1, further comprising:
   generating, by the laser device, the pulsed laser radiation with a wavelength of 300 to 650 nanometers.

9. The method of claim 1, further comprising:
   executing a zigzag scan pattern to create the posterior incision.

10. The method of claim 1, further comprising:
    executing a spiral scan pattern to create the posterior incision.

11. The method of claim 1, further comprising:
    creating the lenticule with a diameter of 6.5 millimeters.

12. The method of claim 1, further comprising:
    creating the lenticule with a thickness of 50 micrometers.

13. The method of claim 1, further comprising:
    creating the anterior channel with a narrower width towards the entrance of the channel and a wider width towards the center of the lenticule.

14. The method of claim 4, further comprising:
    creating the removal incision with a length in a range of a diameter of the lenticule plus or minus 2 millimeters.

* * * * *